United States Patent
Carignano et al.

(10) Patent No.: US 6,313,291 B1
(45) Date of Patent: Nov. 6, 2001

(54) FLUORINATED TRIAZINIC COMPOUNDS

(75) Inventors: Gabriella Carignano; Antonio Russo, both of Milan; Piero Savarino, Turin; Paolo Baratta, Cuneo; Mario Visca, Alessandria, all of (IT)

(73) Assignee: Ausimont S.p.A., Milan (IT)

( * ) Notice: Subject to any disclaimer, the term of this patent is extended or adjusted under 35 U.S.C. 154(b) by 0 days.

(21) Appl. No.: 09/518,174

(22) Filed: Mar. 2, 2000

(30) Foreign Application Priority Data

Mar. 3, 1999 (IT) .......................................... MI99A000426

(51) Int. Cl.[7] ..................... C07D 251/54; C07D 251/70; C08F 20/68
(52) U.S. Cl. ............................. 544/218; 427/258
(58) Field of Search ............................... 544/218; 427/258

(56) References Cited

U.S. PATENT DOCUMENTS

| | | | | |
|---|---|---|---|---|
| 3,981,928 | * | 9/1976 | Pavlik | ................................... 260/615 |
| 4,459,151 | * | 7/1984 | Kuhle et al. | ........................ 544/204 |
| 6,011,135 | * | 1/2000 | Mori | ..................................... 528/423 |

FOREIGN PATENT DOCUMENTS

| | | | |
|---|---|---|---|
| 1 438 617 | * | 5/1966 | (FR) . |
| 1102903 | | 2/1968 | (GB) . |
| 1102015 | | 7/1968 | (GB) . |
| 2 291 439 | * | 1/1996 | (GB) . |
| 2291439 | | 1/1996 | (GB) . |
| 99 05127 | * | 2/1999 | (WO) . |

OTHER PUBLICATIONS

Database Chemlabs, Accession No. 83:149027, XP-002141851, 1974.
Database Chemlabs, Accession No. 96:104198, XP-002141852, 1981.
Database Chemlabs, Accession No. 74:55076, XP-00214853, 1970.
Databse Chemlabs, Accession No. 72:4268, XP-002141854, 1968.
Database Chemlabs, Accession No. 67:99526, XP-002141855, 1966.
Database Chemlabs, Accession No. 4850a, XP-002141856, 1966.
Database Chemlabs, Accession No. 3534h, XP-002141857, 1965.
Database Chemlabs, Accession No. 79:67713, XP-002141858 1972.
Chemical Abstracts, vol. 65, No. 4, 4850a, 1966.
Chemical Abstracts, vol. 64: 3534h, 1965.

* cited by examiner

Primary Examiner—Richard L. Raymond
Assistant Examiner—Venkataraman Balasubramanian
(74) Attorney, Agent, or Firm—Arent Fox Kintner Plotkin & Kahn, PLLC

(57) ABSTRACT

Fluorinated triazinic compounds having the formula:

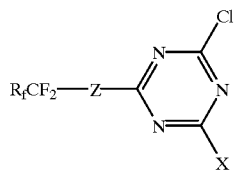

(I)

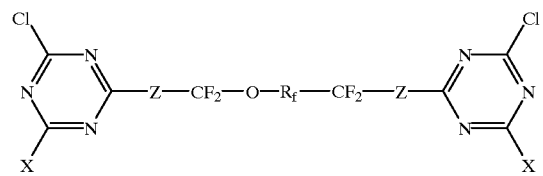

(II)

wherein $Z=T-Y$, with $T=-(CH_2)_q$, $-SO_2$, $-CO$, $q=$ is an integer from 1 to 20; $Y=O-$, $O(C_2H_4O)_p-$, $O(CH_2)_n-NR-$, $O(CH_2)_n-O-$, $O(C_3H_6O)_p-$, $NR-$, $S-$, $S(C_2H_4O)_p-$, $S(C_3H_6O)_p-$; wherein $R=H$, alkyl from 1 to 10 C atoms; n is an integer from 1 to 20; p is an integer from 1 to 5; $R_f$ represents a linear or branched fluoroalkyl chain or a (per)fluoropolyether chain. X is selected from: Cl; $R_f-CF_2-Z$; $CF_3-Z$. Use of these triazinic compounds or of their formulations for the treatment of natural or synthetic fiber textiles.

8 Claims, No Drawings

FLUORINATED TRIAZINIC COMPOUNDS

The present invention relates to products and their formulations for the treatment of natural or synthetic fiber textiles.

More specifically, it relates to products derived from fluorinated compounds able to confer hydro- and oil-repellence characteristics without modifying the textile surface appearance and contemporaneously to give a very good softness, said characteristics being substantially unchanged even after repeated washings with water and solvents.

Textile treatments, specifically cotton, nylon, polyester and mixed textiles comprising the above fibers, to confer hydra- and oil-repellence properties, are known in the prior art. Such treatments are usually carried out by using fluorinated polyacrylates, such as for example Scotchgaurd™ Asahigard™ etc. The drawback of these treatments is that they substantially modify the textile softness and besides the conferred hydra- and oil-repellence are removed through repeated washings, especially with the solvents used in the dry washing.

Tests carried out by the Applicant using fluorinated functional derivatives wherein the fluorinated part derives from a monofunctional perfluoropolyether residue with alcoholic end group show that said treatment does not confer any hydro- and oil-repellence to the textiles.

The need was felt to have available compounds able to confer to textiles high oil- and hydro-repellence without substantially modifying the textile surface appearance and contemporaneously to confer a very good softness, said characteristics remaining substantially unchanged even after repeated washings with water or with solvents.

It has been surprisingly and unexpectedly found by the Applicant that it is possible to solve the above technical problem, i.e., to confer to a substratum constituted by natural or artificial textiles such as cotton, wool, silk, polyester, polyamide or the like, or a combination thereof, hydro- and oil-repellence characteristics which are maintained during the time even after repeated washings also in the presence of solvents, without substantially changing the substratum softness properties, treating the textile with the compounds specified hereinunder.

An object of the present invention are fluorinated triazinic compounds having general formula selected from the following:

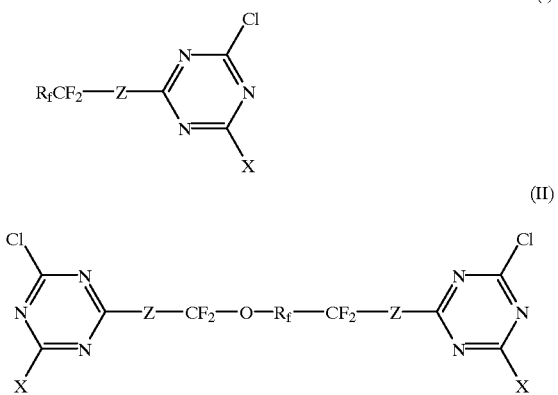

wherein Z=T—Y, wherein:
T=—$(CH_2)_q$—, —$SO_2$—, —CO—, preferably —$(CH_2)_q$—, —$SO_2$—;
q=is an integer from 1 to 20, preferably 1–5;

Y=—O—, —$O(C_2H_4O)_p$—, —$O(CH_2)_n$—NR—, —$O(CH_2)_n$—O—, —$O(C_3H_6O)_p$—, —NR—, —S—, —$S(C_2H_4O)_p$—, —$S(C_3H_6O)_p$—;

wherein R=H, linear or branched alkyl having from 1 to 10 C atoms, preferably 1–4 C atoms;
n=is an integer from 1 to 20, preferably 1–10;
p=is an integer from 1 to 5, preferably 1–3;
$R_f$ represents:
  a linear or branched fluoroalkyl chain, optionally containing heteroatoms, preferably selected from N, O, containing from 1 to 30 C atoms, preferably from 1 to 12 C atoms;
  a (per)fluoropolyether chain comprising repeating units selected from the following:
  a) —(CF($CF_3$)—$CF_2O$)—;
  b) —($CF_2CF_2O$)—;
  c) —(CFLO)—, wherein L=—F, —$CF_3$—,
  d) —$CF_2CF_2CF_2O$—,
  e) —$CH_2CF_2CF_2O$—,
  f) —($CF_2CF(CF_3)O$)—

X is selected from: Cl; $R_f$—$CF_2$—Z; $CF_3$—Z, wherein Z and $R_f$ have the above defined meaning.

When $R_f$ is a perfluoropolyether chain and is monofunctional, then the terminal end is $CF_3O$—, $C_2F_5O$—, $C_3F_7O$—, $Cl(C_3F_6O)$—, $H(C_3F_6O)$—. When $R_f$ is a linear or branched fluoroalkyl chain the end group is $CF_3$—.

Specifically, $R_f$ is of the perfluoropolyether type and has preferably one of the following structures:
1) —$(CF_2O)_a$—$(CF_2CF_2O)_b$— with b/a comprised between 0.3 and 10, extremes included;
2) —$(CF_2$—$CF_2O)_b$—
3) —$(C_3F_6O)_r$—$(C_2F_4O)_b$—$(CFLO)_t$—, with r/b=0.5–2.0 (r+b)/t=10–30
4) —$(OC_3F_6)_r$—$OCF_2(R'_f)_y$—$CF_2O$—$(C_3F_6O)_r$—
5) —$(CF_2CF_2CH_2O)_q$—$OCF_2(R'_f)_y$—O—$(CH_2CF_2CF_2O)_s$— wherein:
L is selected from F, $CF_3$—;
—($C_3F_6O$)— can represent units of formula:

and/or

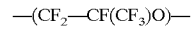

a, b, q, r, s, t, are numbers comprised between 0 and 25, such that the $R_f$ shows number average molecular weight $\overline{M}_n$ values in the range of about 300–5,000, and preferably 300–3,000;
$R'_f$=perfluoroalkylenic group containing from 1 to 4 carbon atoms;
y is 0 or 1.

The most preferred perfluoropolyether chain $R_f$ is selected from the following structures:
—$(CF_2O)_a$—$(CF_2CF_2O)_b$—;
—$(C_3F_6O)_r$—$(C_2F_4O)_b$—$(CFLO)_t$—;
—$(C_3F_6O)_r$—$(CFLO)_t$—;
wherein L and the a, b, r, t indexes have the above mentioned value.

It has been found by the Applicant that Z is a linking group bound to the $R_f$ chain by a chemical stable bond under the application and use conditions of the product and ageing-resistant. The bond between the linking group and the triazine molecule is preferably of ether or amine type, deriving from the nucleophilic substitution of the chlorine in the chlorotriazine with a hydroxyl or amine group.

A process for preparing the compounds of formula (I) and (II) of the present invention requires the reaction of alcohols having the formula:

$$R_f-CF_2-T-YH \quad (III)$$

wherein:
T=—$(CH_2)_q$—, —$SO_2$—, —CO—, preferably —$(CH_2)_q$—, —$SO_2$—;
Y=—O—, —$O(C_2H_4O)_p$—, —$O(CH_2)_n$—O—, —$O(C_3H_6O)_p$—;
the n, p, q indexes have the above mentioned meaning; with a 1,3,5-trichlorotriazine of formula:

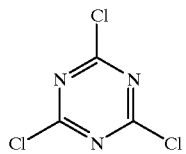

(IV)

The reaction is carried out in an inert solvent able to solubilize the reactants in the reaction conditions, such as for example tetrahydrofurane, dioxane, toluene, xylene, acetone, etc. in the presence of an hydrochloric acid acceptor such as for example sodium or potassium bicarbonate, sodium or potassium carbonate, sodium or potassium hydroxide. Preferably the reaction uses HCl acceptors such as pyridine, 2,6-di-methylpyridine, 2-methylquinoline and 2,4,6-trimethylpyridine (from now on called 2,4,6-collidine or more simply collidine)

For the monosubstituted product, i.e. the invention compounds of formula (I) and (II) wherein X=Cl, the reaction is carried out by gradual addition of the alcohol to a mixture formed by the solvent, the hydrochloric acid acceptor (base) and by the trichlorotriazine. The reaction temperature is in the range 0–10° C.

The bisubstituted products, i.e. the compounds of formula (I) and (II) wherein X is different from Cl, can be obtained in two steps, by using as reaction intermediates the compounds of formula (I) or (II) with X=Cl. The reaction is carried out at a temperature of 30°–40° C. by gradual addition of the alcohol to a mixture constituted by the solvent, by the hydrochloric acid acceptor (base) and by the compounds of formula (I) or (II) with X=Cl.

An equimolecular ratio between the alcohol and the triazinic derivative is required for the reaction, while for the base a light excess, about 10% molar, is required.

The reaction times are of about 3 hours. At the end of the reaction the mixture is filtered to eliminate the precipitated salts during the reaction, and then the product is isolated by stripping the solvent and the base in excess, when the latter is liquid.

Optionally the reaction can be carried out by letting react the trichloro-triazine with the sodium or potassium salt (alcoholate) of the alcohols of formula (III), separately prepared by reaction with bases as known in the prior art.

Generally the reaction is carried out at atmospheric pressure, although the pressure is not critical for the process.

A preparation process of the compounds of formula (I) and (II) wherein Y=—$O(CH_2)_n$—NR—, —NR—, —S—, —$S(C_2H_4O)_p$—, —$S(C_3H_6O)_p$—, is substantially similar to the above described process for the preparation of the compounds wherein Y=—O—, —$O(C_2H_4O)_p$—, —$O(CH_2)_n$—O—, —$O(C_3H_6O)_p$—, starting from the corresponding intermediates.

The textiles preferably treated according to the invention are natural fiber textiles, such as cotton, wool, silk, or the like, or synthetic fiber textiles, such as polyester, polyamide or the like, or combinations thereof.

It has been found by the Applicant that the invention results could be explained, without however to be bound to any theory, by the specific reactivity of these molecules based on the presence of functions able to react with the fiber surface sites by nucleophilic type substitution. In particular the triazinic derivative reactive sites are halogens, in particular chlorine, and the reactive sites on the textiles are generally hydroxyl, thiolic, amine groups.

The treatment can be carried out on the textiles during the finishing or the printing step or also directly on the fiber, optionally in combination with the dyeing step.

The invention compounds are preferably used as formulations, more preferably aqueous formulations. Indeed the Applicant has found that the fluorinated triazinic derivatives of the invention to exert their function are preferably conveyed on the substratum by a formulation. The used formulation must preferably be free from solvents and must guarantee that the reactive triazinic derivative of the invention is adsorbed on the fibers/textiles with the correct conformation, favouring the triazine-surface reaction and limiting the concurrent hydrolysis reaction, since the latter reaction reduces the treatment effectiveness.

The formulation can be constituted by the combination of the fluorinated triazinic derivative with surfactants, preferably hydrocarbon type, such as for example those normally used for the dye formulations; for example ethoxylated alcohols with a different ethoxylation degree or mixtures thereof, etc., can be mentioned. Also anionic surfactants such as for example sodiumdodecylsulphate (SDS) or mixtures of the latter with the above mentioned ethoxylated alcohols can be used.

Another kind of formulation comprises the incorporation of the triazinic derivative in a print paste, characterized in that it contains surfactant in a reduced account. The Applicant has surprisingly found that the best results are obtained by selecting the print pastes among those used to convey reactive dyes on the substratum to be treated. The print pastes are well known in the art of the textile dyes and among those commercially available, pastes for reactive dyes containing for example sodium alginate and pastes for polyacrylate-based acid dyes, can be mentioned.

Both these classes of formulations can optionally contain dyes, obviously chemically compatible, preferably non reactive with the fluorinated triazinic reactive derivative.

The formulation application process preferably takes place at temperatures equal to or lower than the reaction temperature of the triazine reactive groups: for example, derivatives containing a single fluorinated chain $R_f$ are preferably applied at room temperature or lower than room T, while the bisubstituted derivatives, i.e. containing two $R_f$ chains, can be also applied at higher temperatures.

The textiles so treated are preferably subjected to a repeated thermal treatment to guarantee the reaction completion between the-triazinic derivative and the fiber surface. The thermal treatment is generally carried out at temperatures in the range 90–160° C., compatibly with the kind of the fiber to be treated; the treatment times are comprised between 5 and 30 minutes. The used amount of the triazinic compounds of the invention changes depending on the type and the characteristics of the substratum and it is generally in the range 0.1–20% by weight of the total weight of the fiber and preferably 1–10% by weight.

As already said the textiles treated with the compounds and/or formulations of the invention, resist the washing with water or with solvents even after several washings. As washing solvents, acetone, which is a good solvent for the components of the formulations and in particular for the fluorinated triazines, can for example be mentioned. The fact that the treated textiles resist the washing with acetone is a demonstration of the formation of a chemical bond between the compounds of the invention and the textiles.

The following Examples are given for illustrative purposes of the invention but they are not limitative of the scope of the same.

EXAMPLES

Sinthesis of the Derivatives of the Invention

The product structure has been confirmed by IR, $^1$H-NMR, $^{19}$F-NMR, $^{13}$C-NMR analyses.

Example 1
Preparation of the compound of formula:

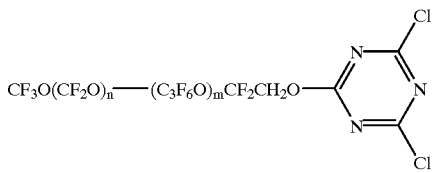

In a 2 l glass flask, equipped with mechanical stirring, thermometer and dropping funnel, 1000 g (870 cc) of toluene, 28.4 g (0.15 moli) of 2,4,6-trichlorotriazine and 20 g (0.165 moles) of 2,4,6-collidine are introduced. The mixture is cooled to 0° C. and then 100 g (0.15 moles) of $CF_3O(CF_2O)_n$—$(C_3F_6O)$—$_mCF_2$—$CH_2OH$ (average equivalent weight EW=650) are slowly dropped under stirring, maintaining the temperature inside the flask between 0° C. and 10° C.

When the alcohol dropping is over, the reaction mixture is let reach the room temperature and then under stirring under these conditions for about 2 hours. The precipitated collidine chlorohydrate is then removed from the reaction mixture by filtering. The solvent and the collidine in excess are then distilled from the product at 80–100° C./1 mmHg.

The so obtained product appears cloudy and it is then subjected to a second filtering by 0.2 $\mu$ filter. 107.9 g of product are obtained.

Example 2
Preparation of the compound of formula:

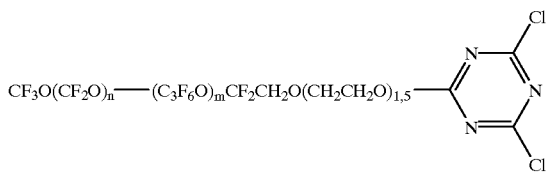

By operating under the same conditions described in Example 1, 100 g (0.14 moles) of $CF_3O(CF_2O)_n$—$(C_3F_6O)_m$ $CF_2CH_2O$—$(CH_2CH_2O)_{1.5}H$ (EW=716), are let react with 25.77 g (0.14 moles) of 2,4,6-trichlorotriazine and 18.6 q (0.15 moles) of 2,4,6-collidine, in 1000 g of toluene. 105.3 g of product are obtained.

Example 3
Preparation of the compound of formula:

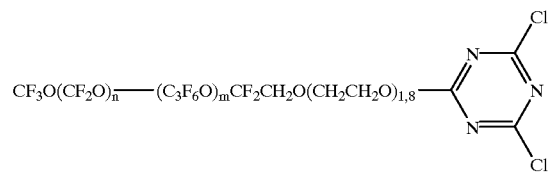

By operating under the same conditions described in Example 1, 100 g (0.137 moles) of $CH_3O(CF_2O)_n$—$(C_3F_6O)_mCF_2CH_2O$—$(CH_2CH_2O)_{1.8}H$ (EW=729), are let react with 25.3 g (0.137 moles) of 2,4,6-trichlorotriazine and 18.2 g (0.15 moles) of 2,4,6-collidine, in 1000 g of toluene. 110.7 g of product are obtained.

Example 4
Preparation of the compound of formula:

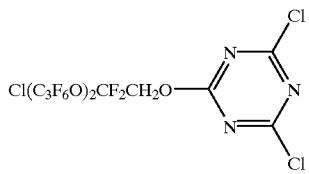

In a 2 l glass flask, equipped with mechanical stirring, thermometer and dropping funnel, 1000 g (870 cc) of toluene, 41.3 g (0.225 moles) of 2,4,6-trichlorotriazine and 29.6 g (0.245 moles) of 2,4,6-collidine are introduced. The mixture is cooled to 0° C. and then 100 g (0.223 moles) of $Cl(C_3F_6O)_2CF_2$—$CH_2OH$ are slowly dropped under stirring, maintaining the temperature inside the flask between 0° C. and 10° C. When the alcohol dropping is over, the reaction mixture is let reach the room temperature and then under stirring under these conditions for about 2 hours.

The precipitated collidine chlorohydrate is then removed from the reaction mixture by filtering. The solvent and the collidine in excess are then distilled from the product at a temperature of 80–100° C. and at the pressure of 1 mmHg. The so obtained product results cloudy and is then subjected to a second filtering by 0.2 $\mu$ filter. 123 g of product are obtained.

Example 5
Preparation of the compound of formula:

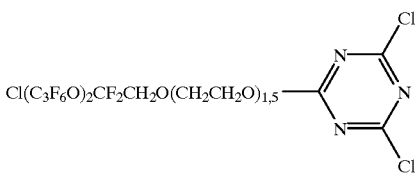

By operating under the same conditions described in Example 1, 114.2 g (0.22 moles) of $Cl(C_3F_6O)_2CF_2CH_2O$ $(CH_2CH_2O)_{1.5}H$ are let react with 41.3 g (0.225 moles) of 2,4,6-trichlorotriazine and 29.6 g (0.245 moles) of 2,4,6-collidine, in 1000 g of toluene. 144.6 g of product are obtained.

Example 6
Preparation of the compound of formula:

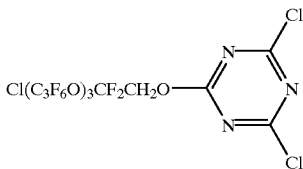

By operating under the same conditions described in Example 1, 100 g (0.16 moles) of $Cl(C_3F_6O)_3CF_2CH_2OH$, are let react with 29.5 g (0.16 moles) of 2,4,6-trichlorotriazine and 21.3 g (0.18 moles) of 2,4,6-collidine, in 1000 g of toluene. 109.5 g of product are obtained.

Example 7
Preparation of the compound of formula:

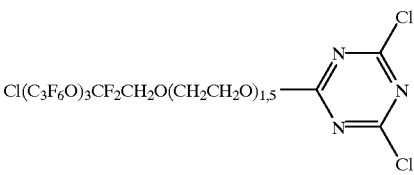

By operating under the same conditions described in Example 1, 100 g (0.147 moles) of $Cl(C_3F_6O)_3CF_2CH_2O(Ch_2CH_2O)_{1.5}H$, are let react with 27 g (0.147 moles) of 2,4,6-trichlorotriazine and 19.5 g (0.16 moles) of 2,4,6-collidine, in 1000 g of toluene. 110 g of product are obtained.

Example 8
Preparation of the compound of formula:

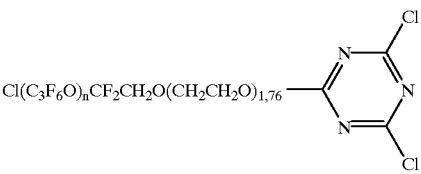

wherein n=2–5.

By operating under the same conditions described in Example 1, 50 g (0.08 moles) of $Cl(C_3F_6O)_nCF_2CH_2O(Ch_2CH_2O)_{1.76}H$ (EW=613), are let react with 14.9 g (0.08 moles) of 2,4,6-trichlorotriazine and 10.5 g (0.086 moles) of 2,4,6-collidine, in 260 g of toluene. 53.5 g of product are obtained.

Example 9
Preparation of the compound of formula:

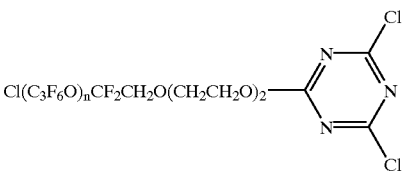

wherein n=2–5.

By operating under the same conditions described in Example 1, 100 g (0.16 moles) of $Cl(C_3F_6O)_nCF_2CH_2O(Ch_2CH_2O)_2H$ (n=2–5, EW=623) are let react with 29.6 g (0.16 moles) of 2,4,6-trichlorotriazine and 21.3 g (0.176 moles) of 2,4,6-collidine, in 1000 g of toluene. 112.4 g of product are obtained.

Example 10
Preparation of the compound of formula:

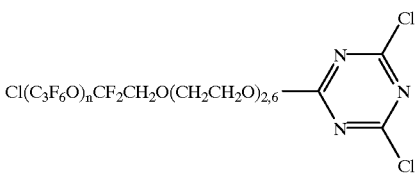

wherein n=2–5.

By operating under the same conditions described in Example 1, 100 g (0.15 moles) of $Cl(C_3F_6O)_nCF_2CH_2O(Ch_2CH_2O)_{2.6}H$ (n=2–5, EW=649) are let react with 28.4 g (0.15 moles) of 2,4,6-trichlorotriazine and 19.9 g (0.16 moles) of 2,4,6-collidine, in 1000 g of toluene. 105.3 g of product are obtained.

Example 11
Preparation of the compound of formula:

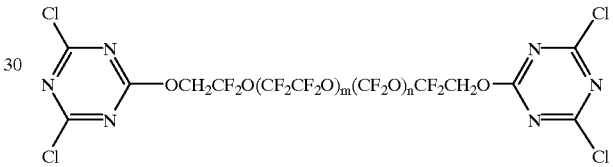

By operating under the same conditions described in Example 1, 100 g (0.16 eq) of $HOCH_2CF_2O(CF_2CF_2O)_m(CF_2O)_nCF_2CH_2OH$ (EW=605), are let react with 30.2 g (0.16 moles) of 2,4,6-trichlorotriazine and 22 g (0.18 moles) of 2,4,6-collidine, in 595 g of toluene. 106 g of product are obtained.

Example 12
Preparation of the compound of formula:

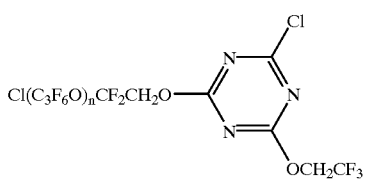

In a 1 l glass flask, equipped with mechanical stirring, thermometer and dropping funnel, 300 g of toluene, 16.76 g (0.09 moles) of 2,4,6-trichlorotriazine and 12.1 g (0.1 moles) of 2,4,6-collidine are introduced. The mixture is cooled to 0° C. and then 50 g (0.09 moles) of $Cl(C_3F_6O)_nCF_2CH_2OH$ (n=2–5, EW=539), are slowly dropped under stirring, maintaining the temperature inside the flask between 0° C. and 10° C. When the alcohol dropping is over, the reaction mixture is let reach the room temperature and then under stirring under these conditions for about 2 hours. The precipitated collidine chlorohydrate is then removed from the reaction mixture by filtering. To the filtered mixture reaction 12.1 g (0.1 moles) of 2,4,6-collidine are then added. The temperature is then brought to 30° C. and then, by dropping under stirring, 9.16 g (0.09 moles) of $CF_3CH_2OH$ are added. When the addition is over, the reaction is let continue for about 2 hours.

The precipitated collidine chlorohydrate is then removed from the reaction mixture by filtering. The solvent and the collidine in excess are then distilled from the product at 80–100° C./1 mmHg.

The so obtained product appears cloudy and is then subjected to a second filtering by $0.2\mu$ filter. 53.2 g of product are obtained.

Application Examples

Characterization

Hydro-repellence Yest

The test is carried out by contacting for 10 seconds the textiles with drops of a water/isopropanol hydroalcoholic mixture (IPA) at concentration increasing in alcohol, using at last a drop of pure alcohol. After drop removal, it is observed if the liquid leaves a surface halo or if it penetrates the weft. The attributed hydro-repellence value (rating) is the number which corresponds to the liquid which is neither penetrated nor has left halos on the textiles.

| Rating | Water/IPA mixture (% by wt) |
|---|---|
| W | 100/0 |
| 1 | 90/10 |
| 2 | 80/20 |
| 3 | 70/30 |
| 4 | 60/40 |
| 5 | 50/50 |
| 6 | 40/60 |
| 7 | 30/70 |
| 8 | 20/80 |
| 9 | 10/90 |
| 10 | 0/100 |

The notation W means that the sample resists the pure water only.

Oil-repellence Test

The test is carried out according to the method AATCC Standard test 118-1978, wherein the resistance given from the textiles to the penetration of a drop of oils having different surface tension is evaluated. The drop is contacted with the textiles for 30 seconds and then removed. It is observed if the oil leaves a surface halo or if it penetrates the weft. The attributed oil-repellence value is the number which corresponds to the oil which is neither penetrated nor has left halos on the textiles.

| Rating | type of oil |
|---|---|
| 1 | vaseline oil |
| 2 | vaselin oil/ n-hexadecane 65/35 |
| 3 | n-hexadecane |
| 4 | n-tetradecane |
| 5 | n-dodecane |
| 6 | n-decane |
| 7 | n-octane |
| 8 | n-heptane |

Example 13

Cotton Treatment

Preparation of the Fluorinated Chlorotriazine Dispersion

The fluorinated chlorotriazine described in Example 3 is mixed at 3% concentration with a print paste (PASTE 1) for reactive dyestuffs having the following composition:
PASTE I
aqueous dispersion at 7% of sodium alginate (50%)
urea (12%)
aqueous solution at 25% of sodium benzensulphonate (6%)
potassium carbonate (2%)
water (30%).

Textile Treatment

The so obtained formulation is applied at room temperature on a cotton cloth having 10 cm×10 cm sizes by using a doctor, following the conventional application procedures of the print pastes. Various cloths are treated with various doctor passages (from 1 to 4).

The textiles are repeatedly subjected to thermal treatment to guarantee the reactive fixing to the fiber: the treatment is carried out in a stove at 140–160° C. for 10–15 minutes.

After the thermal treatment the textiles are washed in linitest equipment according to the following standard washing procedure:

The cloths are placed in a stainless steel container containing 10 steel balls (0.6 cm diameter), in the presence of a solution at 5 g/l of surfactant with a solution/textile weight ratio (bath ratio) of 40. The container is thermostated at 60° C. and continuously stirred for 60 minutes.

The cloths are rinsed with water until foaming disappearance. After drying, on the treated cloths a first hydro- and oil-repellence evaluation is carried out as previously reported.

In order to simulate the dry washing, and in case eliminate the reactive and/or surfactant excess, some cloths are subjected to additional washings with solvent.

After drying, the cloths are subjected to further hydro- and oil-repellence tests.

In Table 1 the results of the tests in connection with the number and kind of washings and the amount of active principle deposited on the cloth are reported.
The results are reported in Table 1:

TABLE 1

| Doctor passages N° | Active principle (% by wt) on fiber) | Linitest washing | | I Acetone washing | | II Acetone washing | |
|---|---|---|---|---|---|---|---|
| | | Wr | Or | Wr | Or | Wr | Or |
| 1 | 1 | 3 | 4 | 3 | 4 | 3 | 3 |
| 1 | 2.4 | 4 | 5 | 5 | 5 | 5 | 5 |
| 1 | 4.3 | 4 | 5 | 4 | 5 | 4 | 5 |
| 4 | 2.5 | 2 | 6 | 6 | 6 | 6 | 5 |
| 4 | 4.9 | 2 | 5 | 6 | 5 | 6 | 5 |
| 4 | 7.1 | 2 | 6 | 6 | 6 | 6 | 6 |

The textiles result soft.

Example 14

Cotton Treatment

The fluorinated chlorotriazine described in Example 2 is mixed at 3% concentration with a print paste (PASTE 1) for reactive dyestuffs as described in Example 13.

The so obtained formulation is applied on cotton cloths according to the procedures described in Example 13. The cloths are then washed as described in Example 13 and subjected to the hydro- and oil-repellence tests.

The results are reported in Table 2.

TABLE 2

| Doctor passages | Active principle (% by wt) | Linitest washing | | I Acetone washing | | II Acetone washing | |
|---|---|---|---|---|---|---|---|
| N° | on fiber) | Wr | Or | Wr | Or | Wr | Or |
| 1 | 4 | — | — | 5 | 5 | 5 | 5 |

The textiles result soft.

Example 15

Cotton Treatment

The fluorinated chlorotriazine described in Example 1 is mixed at 3% concentration with a print paste (PASTE 1) for reactive dyestuffs as described in Example 13.

The so obtained formulation is applied on cotton cloths according to the procedures described in Example 13. The cloths are then washed as described in Example 13 and subjected to the hydro- and oil-repellence tests.

The results are reported in Table 3.

TABLE 3

| Doctor passages | Active principle (% by wt) | Linitest washing | | I Acetone washing | | II Acetone washing | |
|---|---|---|---|---|---|---|---|
| N° | on fiber) | Wr | Or | Wr | Or | Wr | Or |
| 1 | 4 | — | — | 3 | 4 | 3 | 4 |

The textiles result soft.

Example 16

Cotton Treatment

The compound described in Example 2 previously dissolved in acetone is dispersed in water by using an hydrocarbon surfactant Brij 56 with a surfactant/triazine weight ratio equal to 1.

The dispersion pH is brought to 8 with a sodium bicarbonate solution. A series of cotton cloths are treated by dipping in a bath containing the dispersion maintained at room temperature and under stirring for periods ranging from 5 to 30 minutes. The treated cloths are subjected to thermal treatment at 120° C. for 15 minutes and they are successively subjected to the washing procedures as described in Example 13.

The hydro- and oil-repellence test results are reported in Table 4:

TABLE 4

| Treatment time (min) | Active principle (% by wt) on fiber) | Linitest washing | | I Acetone washing | | II Acetone washing | |
|---|---|---|---|---|---|---|---|
| | | Wr | Or | Wr | Or | Wr | Or |
| 5 | 2 | — | — | 3 | 5 | 3 | 5 |
| 20 | 4 | — | — | 3 | 5 | 3 | 5 |

The textiles result soft.

Example 17

Cotton Treatment

The fluorinated chlorotriazine described in Example 7 is mixed at 3% concentration with a print paste (PASTE 1) for reactive dyestuffs as described in Example 13.

The so obtained formulation is applied on cotton cloths according to the procedures described in Example 13. The cloths are then washed as described in Example 13 and subjected to the hydro- and oil-repellence tests.
The results are reported in Table 5.

TABLE 5

| Doctor passages | Active principle (% by wt) | Linitest washing | | I Acetone washing | | II Acetone washing | |
|---|---|---|---|---|---|---|---|
| N° | on fiber) | Wr | Or | Wr | Or | Wr | Or |
| 1 | 4 | — | — | 4 | 3 | 4 | 3 |

The textiles result soft.

Example 18

Cotton Treatment

The fluorinated chlorotriazine described in Example 8 is mixed at 3% concentration with a print paste (PASTE 1) for reactive dyestuffs as described in Example 13.

The so obtained formulation is applied on cotton cloths according to the procedures described in Example 13. The cloths are then washed as described in Example 13 and subjected to the hydro- and oil-repellence tests.
The results are reported in Table 6:

TABLE 6

| Doctor passages | Active principle (% by wt) | Linitest washing | | I Acetone washing | | II Acetone washing | |
|---|---|---|---|---|---|---|---|
| N° | on fiber) | Wr | Or | Wr | Or | Wr | Or |
| 4 | 1.8 | 2 | 2 | 2 | 2 | 2 | 2 |
| 4 | 3.8 | 3 | 3 | 3 | 2 | 3 | 2 |
| 4 | 5.6 | 3 | 3 | 3 | 2 | 3 | 2 |
| 4 | 6.7 | 1 | 2 | 3 | 2 | 3 | 2 |

The textiles result soft.

Example 19

Cotton Treatment

The fluorinated chlorotriazine described in Example 9 is mixed at 3% concentration with a print paste (PASTE 1) for reactive dyestuffs as described in Example 13.

The so obtained formulation is applied on cotton cloths according to the procedures described in Example 13. The cloths are then washed as described in Example 13 and subjected to the hydro- and oil-repellence tests.
The results are reported in Table 7:

TABLE 7

| Doctor passages N° | Active principle (% by wt) on fiber | Linitest washing Wr | Linitest washing Or | I Acetone washing Wr | I Acetone washing Or | II Acetone washing Wr | II Acetone washing Or |
|---|---|---|---|---|---|---|---|
| 4 | 5.9 | W | 5 | 3 | 4 | 3 | 3 |
| 4 | 7.6 | 1 | 4 | 3 | 4 | 3 | 3 |
| 4 | 8.8 | 1 | 4 | 4 | 4 | 4 | 4 |
| 4 | 12.8 | 1 | 4 | 4 | 4 | 4 | 4 |

The textiles result soft.

Example 20

Cotton Treatment

The fluorinated chlorotriazine described in Example 10 is mixed at 3% concentration with a print paste (PASTE 1) for reactive dyestuffs as described in Example 13.

The so obtained formulation is applied on cotton cloths according to the procedures described in Example 13. The cloths are then washed as described in Example 13 and subjected to the hydro- and oil-repellence tests.
The results are reported in Table 8:

TABLE 8

| Doctor passages N° | Active principle (% by wt) on fiber | Linitest washing Wr | Linitest washing Or | I Acetone washing Wr | I Acetone washing Or | II Acetone washing Wr | II Acetone washing Or |
|---|---|---|---|---|---|---|---|
| 4 | 6 | 0 | 4 | 2 | 3 | 2 | 2 |
| 4 | 7.6 | 0 | 4 | 3 | 4 | 4 | 3 |
| 4 | 8.8 | W | 4 | 3 | 3 | 3 | 3 |
| 4 | 12.5 | 1 | 4 | 3 | 3 | 4 | 3 |

The textiles result soft.

Example 21

Wool Treatment

The fluorinated chlorotriazine described in Example 3 is mixed at 3° concentration with a print paste (PASTE 1) for reactive dyestuffs as described in Example 13.

The so obtained formulation is applied on wool textiles and wool cloth according to the procedures described in Example 13. The cloths are then washed as described in Example 13 and subjected to the hydro- and oil-repellence tests.
The results are reported in Table 9:

TABLE 9

| Sub-stratum kind | Active principle (% by wt) on fiber | Linitest washing Wr | Linitest washing Or | I Acetone washing Wr | I Acetone washing Or | II Acetone washing Wr | II Acetone washing Or |
|---|---|---|---|---|---|---|---|
| cloth | 5 | 6 | 6 | 7 | 5 | 8 | 5 |
| cloth | 12 | 6 | 6 | 7 | 5 | 8 | 5 |

TABLE 9-continued

| Sub-stratum kind | Active principle (% by wt) on fiber | Linitest washing Wr | Linitest washing Or | I Acetone washing Wr | I Acetone washing Or | II Acetone washing Wr | II Acetone washing Or |
|---|---|---|---|---|---|---|---|
| textiles | 6 | 3 | 5 | 6 | 4 | 6 | 4 |
| textiles | 8 | 2 | 5 | 4 | 4 | 4 | 4 |

The textiles result soft and the textile appearance is not substantially modified.

Example 22

Wool Treatment

A fluorinated triazinic derivative having a structure as described in Example 3 is introduced at 5% concentration in a print paste (PASTE II) constituted by:
Carbopol Printrite 2491 WCS (6% by weight)
Urea (10%)
Potassium carbonate (3%)
Water (81%)
and applied as described in Example 13 on wool textiles.

After treatment, the textiles are subjected to washing as described in Example 13 and subjected to hydro- and oil-repellence tests.
The results are reported in Table 10:

TABLE 10

| Doctor passages N° | Active principle (% by wt) on fiber | Linitest washing Wr | Linitest washing Or | I Acetone washing Wr | I Acetone washing Or | II Acetone washing Wr | II Acetone washing Or |
|---|---|---|---|---|---|---|---|
| 1 | 5 | 3 | — | 3 | — | 3 | — |

The textiles result soft and the textile appearance is not substantially modified.

Example 23

Linen Treatment

A fluorinated triazinic derivative having a structure as described in Example 3 and formulated in the paste I (Example 13) and in the paste II (Example 22) is applied as described in Example 13 on linen textiles.

After treatment, the textiles are washed as described in Example 13 and subjected to the hydro- and oil-repellence tests. The results are reported in Table 11:

TABLE 11

| Paste type | Active principle (% by wt) on fiber | Linitest washing Wr | Linitest washing Or | I Acetone washing Wr | I Acetone washing Or | II Acetone washing Wr | II Acetone washing Or |
|---|---|---|---|---|---|---|---|
| I | 9 | 2 | 6 | 3 | 6 | 3/4 | 5/6 |
| II | 8 | 3 | 5 | 4 | 4 | 4 | 4 |

The textiles result soft; the textile appearance is not substantially modified.

Example 24

Silk Treatment

A fluorinated triazinic derivative having a structure as described in Example 3 is formulated at 2% concentration in a commercial print paste having an acrylic base Serviprint 7501 (PASTE III) having the following composition by weight:

PASTE III

Aqueous dispersion at 8% of SERVIPRINT 7501 (60%)
Glycerine (3%)
Urea (6%)
Solution at 33% of $(NH_4)_2SO_4$ (5%)
Water (26%)

The so obtained formulation is then applied as described in Example 13 on silk textiles. Before the treatment, the silk textiles are basified by imbibition with a sodium carbonate solution.

After treatment, the textiles are subjected to washing as described in Example 13 and subjected to hydro- and oil-repellence tests.

The results are reported in Table 12:

TABLE 12

| Paste type | Active principle (% by wt) on fiber | Linitest washing | | I Acetone washing | | II Acetone washing | |
|---|---|---|---|---|---|---|---|
| | | Wr | Or | Wr | Or | Wr | Or |
| III | 6 | 2 | 5 | 3 | 5 | 3 | 5 |

The textiles result soft.

Example 25

Comparative

A fluorinated alcohol having the structure of the reactant used for the preparation of the Example 3 triazinic derivative is dispersed by an hydrocarbon surfactant as described in Example 16 and applied on a cotton cloth as described in Example 16 at the concentration of 5% by weight with respect to the fiber. After the treatment and the washings as described in Example 13, the hydro- and oil-repellence measurements show how the treatment does not confer any hydro- and oil-repellence characteristic to the substratum (Wr=0, Or=0).

Example 26

Comparative

The print pastes PASTE I, PASTE II, PASTE III previously described in Examples 13, 22, 24 respectively are applied as described in Examples 13, 22, 24 respectively, in absence of the fluorinated triazinic derivative. As it is noticed from the results reported in Table 13, the treatment does not confer to the textiles any hydro- and oil-repellence properties.

TABLE 13

| Paste type | Cloth type | Linitest washing | | I Acetone washing | | II Acetone washing | |
|---|---|---|---|---|---|---|---|
| | | Wr | Or | Wr | Or | Wr | Or |
| I | cotton | 0 | 0 | 0 | 0 | 0 | 0 |
| II | linen | 0 | 0 | 0 | 0 | 0 | 0 |
| III | silk | 0 | 0 | 0 | 0 | 0 | 0 |

What is claimed is:

1. Flourinated triazinic compounds having a formula, selected from the following:

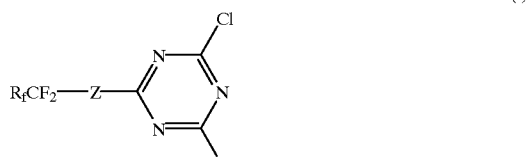

(I)

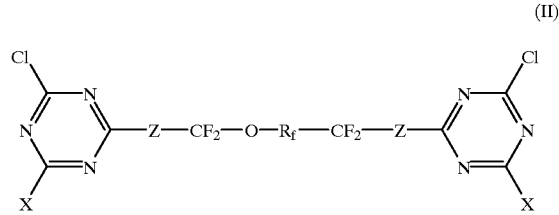

(II)

wherein Z=T—Y, wherein:
T=—$(CH_2)_q$—, —$SO_2$—, —CO—;
q is an integer from 1 to 20;
Y=—O—, —$O(C_2H_4O)_p$—, —$O(CH_2)_n$—NR—, —$O(CH_2)n$—O—, —$O(C_3H_6O)_p$—, —NR—, —S—, —$S(C_2H_4O)_p$—, —$S(C_3H_6O)_p$—;
wherein R=H, alkyl having from 1 to 10 C atoms, linear or branched;
n is an integer from 1 to 20;
p is an integer from 1 to 5;
$R_f$ represents:
  a linear or branched fluoroalkyl chain having —$CF_3$ end groups, optionally containing heteroatoms selected from N, O, containing from 1 to 30 C atoms, provided that $R_f$ is not a fluoroalkyl group in formula (I); or
  a (per)fluoropolyether chain comprising repeating units selected from the following:
    a) —$(CF(CF_3)$—$CF_2O)$—,
    b) —$(CF_2CF_2O)$—,
    c) —(CFLO)—, wherein L=—F, —$CF_3$,
    d) —$CF_2CF_2CF_2O$—,
    e) —$CH_2CF_2CF_2O$—,
    f) —$CF_2CF(CF_3)O$—
  the (per)fluoropolyether chain having end groups selected from $CF_3O$—, $C_2F_5O$—, $C_3F_7O$—, $Cl(C_3F_6O)$—, $H(C_3F_6O)$— and showing number average molecular weight $\overline{M}_n$ values in the range of about 300–5,000; and
X is selected from: Cl; $R_f$—$CF_2$—Z; $CF_3$—Z, wherein Z and $R_f$ have the above defined meaning.

2. Fluorinated triazinic compounds according to claim 1, wherein $R_f$ is a perfluoropolyether and has one of the following units:
1) —$(CF_2O)_a$—$(CF_2CF_2O)_b$— with b/a between 0.3 and 10, extremes included;
2) —$(CF_2$—$CF_2O)_b$—;
3) —$(C_3F_6O)_r$—$(C_2F_4O)_b$—$(CFLO)_t$— with r/b=0.5–2.0 and (r+b)/t=10–30;
4) —$(OC_3F_6)_r$—$OCF_2(R'_f)_y$—$CF_2O$—$(C_3F_6O)r$—;
5) $(CF_2CF_2CH_2O)_q$—$OCF_2(R'_f)_y$—O—$(CH_2CF_2CF_2O)_s$—wherein
L is selected from —F, —$CF_3$;
a, b, q, r, s, t are numbers in the range 0–25, such that $R_f$ shows number average molecular weight $\overline{M}_n$ values as defined above;

R'$_f$=perfluoroalkylene group containing from 1 to 4 carbon atoms; and y is 0 or 1.

3. Fluorinated triazinic compounds according to claim 1 wherein R$_f$ is a perfluoropolyether chain selected from the following structures:

—(CF$_2$O)$_a$—(CF$_2$CF$_2$O)$_b$—;
—(C$_3$F$_6$O)$_r$—(C$_2$F$_4$O)$_b$—(CFLO)$_t$—;
—(C$_3$F$_6$O)$_r$—(CFLO)$_t$—;

wherein L and the a, b, r, t indexes have the above mentioned value.

4. A process for preparing fluorinated triazinic compounds having the general formula (I):

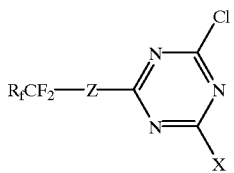

(I)

wherein Z=T—Y, wherein:
T=—(CH$_2$)$_q$—, —SO$_2$—, —CO—;
q is an integer from 1 to 20;
Y=—O—, —O(C$_2$H$_4$O)$_p$—, —O(CH$_2$)$_n$—NR—, —O(CH$_2$)n—O—, —O(C$_3$H$_6$O)$_p$—, —NR—, —S—, —S(C$_2$H$_4$O)$_p$—, —S(C$_3$H$_6$O)$_p$—;
wherein R=H, alkyl having from 1 to 10 C atoms, linear or branched;
n is an integer from 1 to 20;
p is an integer from 1 to 5;
R$_f$ represents:
  a linear or branched fluoroalkyl chain having —CF$_3$ end groups, optionally containing heteroatoms selected from N, O, containing from 1 to 30 C atoms, provided that R$_f$ is not a fluoroalkyl group in formula (I); or
  a (per)fluoropolyether chain comprising repeating units selected from the following:
    a) —(CF(CF$_3$)—CF$_2$O)—,
    b) —(CF$_2$CF$_2$O)—,
    c) —(CFLO)—, wherein L=—F, —CF$_3$,
    d) —CF$_2$CF$_2$CF$_2$O—,
    e) —CH$_2$CF$_2$CF$_2$O—,
    f) —CF$_2$CF(CF$_3$)O—
    the (per)fluoropolyether chain having end groups CF$_3$O—, C$_2$F$_5$O—, C$_3$F$_7$O—, Cl(C$_3$F$_6$O)—, H(C$_3$F$_6$O)— and showing number average molecular weight $\overline{M}_n$ values in the range of about 300–5,000; and
X is selected from: Cl; R$_f$—CF$_2$—Z; CF$_3$—Z, wherein Z and R$_f$ have the above defined meaning;

said process comprising the reaction of at least one alcohol having the formula:

R$_f$CF$_2$—T—YH  (III)

wherein:
T=—(CH$_2$)$_q$—, —SO$_2$—, —CO—, preferably —(CH$_2$)$_q$—, —SO$_2$—;
Y=—O—, —O(C$_2$H$_4$O)$_p$—, —O(CH$_2$)$_n$—O—, —O(C$_3$H$_6$O)$_p$—;
the n, p, q indexes have the above mentioned meaning;
with a 1,3,5-trichlorotriazine of formula:

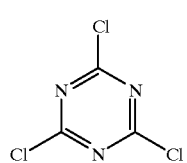

(IV)

wherein the ratio between the alcohol and the trichlorotriazine of formula (IV) is equimolar; the hydrochloric acid acceptor is present in a 10% molar excess, wherein the reaction temperature for the compounds of formula (I) and (II), wherein X=Cl, is in the range of 0–10° C.

5. A process according to claim 4, wherein the reaction is carried out in an inert solvent selected from tetrahydrofurane, dioxane, toluene, xylene, acetone, and in the presence of an hydrochloric acid acceptor selected from sodium bicarbonate, potassium bicarbonate, sodium carbonate, potassium carbonate, sodium hydroxide, potassium hydroxide, pyridine, 2,6-dimethylpyridine, 2-methylquinoline and 2,4,6-trimethylpyridine.

6. A process according to claim 4, wherein the compounds of formula (I) and (II) wherein X is not Cl, are obtained by reacting in an inert solvent, the alcohol with the compound of formula (I) or (II) with X=Cl in the presence of a hydrochloric acid acceptor.

7. Formulations comprising the fluorinated triazinic compounds according to claim 1 and hydrocarbon surfactants selected from ethoxylated alcohols with a different ethoxylation degree or mixtures thereof.

8. Formulations comprising the fluorinated triazinic compounds according to claim 1 and a print paste for textile dyeing.

* * * * *